US010945965B2

(12) United States Patent
Pottier et al.

(10) Patent No.: US 10,945,965 B2
(45) Date of Patent: Mar. 16, 2021

(54) NANOPARTICLES COMPRISING METALLIC AND HAFNIUM OXIDE MATERIALS, PREPARATION AND USES THEREOF

(71) Applicant: NANOBIOTIX, Paris (FR)

(72) Inventors: Agnes Pottier, Paris (FR); Laurent Levy, Paris (FR); Marie-Edith Meyre, Paris (FR)

(73) Assignee: NANOBIOTIX, Paris (FR)

( * ) Notice: Subject to any disclaimer, the term of this patent is extended or adjusted under 35 U.S.C. 154(b) by 803 days.

(21) Appl. No.: 14/364,859

(22) PCT Filed: Dec. 17, 2012

(86) PCT No.: PCT/EP2012/075731
§ 371 (c)(1),
(2) Date: Jun. 12, 2014

(87) PCT Pub. No.: WO2013/087920
PCT Pub. Date: Jun. 20, 2013

(65) Prior Publication Data
US 2014/0335015 A1 Nov. 13, 2014

Related U.S. Application Data

(60) Provisional application No. 61/576,437, filed on Dec. 16, 2011.

(30) Foreign Application Priority Data

Dec. 16, 2011 (EP) .................................... 11193968

(51) Int. Cl.
A61K 33/24 (2019.01)
A61K 41/00 (2020.01)
A61K 49/00 (2006.01)
A61K 49/04 (2006.01)
A61K 51/12 (2006.01)
A61N 5/10 (2006.01)
A61K 9/51 (2006.01)
A61K 9/00 (2006.01)

(52) U.S. Cl.
CPC .......... A61K 9/5115 (2013.01); A61K 9/0009 (2013.01); A61K 9/51 (2013.01); A61K 33/24 (2013.01); A61K 41/0038 (2013.01); A61K 41/0052 (2013.01); A61K 49/00 (2013.01); A61K 49/04 (2013.01); A61K 51/1244 (2013.01); A61N 5/10 (2013.01); A61K 2123/00 (2013.01)

(58) Field of Classification Search
None
See application file for complete search history.

(56) References Cited

U.S. PATENT DOCUMENTS

| 4,280,918 A | 7/1981 | Homola et al. |
| 4,672,040 A | 6/1987 | Josephson |
| 4,770,183 A | 9/1988 | Groman et al. |
| 5,225,212 A | 7/1993 | Martin et al. |
| 5,370,901 A | 12/1994 | Tournier et al. |
| 5,395,619 A | 3/1995 | Zalipsky et al. |
| 5,582,172 A | 12/1996 | Papisov et al. |
| 6,200,598 B1 | 3/2001 | Needham |
| 6,251,365 B1 | 6/2001 | Bäuerlein et al. |
| 6,514,481 B1 | 2/2003 | Prasad et al. |
| 6,541,039 B1 | 4/2003 | Lesniak et al. |
| 6,726,925 B1 | 4/2004 | Needham |
| 6,955,639 B2 | 10/2005 | Hainfeld et al. |
| 7,367,934 B2 | 5/2008 | Hainfeld et al. |
| 7,427,393 B2 | 9/2008 | Takeyama |
| 8,845,507 B2 | 9/2014 | Levy et al. |
| 2003/0125283 A1 | 7/2003 | Gatenby |
| 2004/0181114 A1 | 9/2004 | Hainfeld et al. |
| 2004/0208825 A1 | 10/2004 | Carpenter et al. |

(Continued)

FOREIGN PATENT DOCUMENTS

| DE | 10 2006 041495 | 3/2008 |
| DE | 10 2008 008522 | 8/2009 |

(Continued)

OTHER PUBLICATIONS

Jain, S., et al., "Cell-Specific Radiosensitization by Gold Nanoparticles at Megavoltage Radiation Energies", Int. J. Radiation Oncology Biol. Phys., 2011, pp. 531-539.*
Understandingnano, "Nanoparticles for enhanced x-ray treatment of cancer tumors", accessed from: http://www.understandingnano.com/nanomedicine-nanoparticle-xray-cancer-treatment.html; Jul. 2009, pp. 1-2.*
Greish, K., et al., "Enhanced Permeability and Retention (EPR) Effect for Anticancer Nanomedicine Drug Targeting", Cancer Nanotech., pp. 25-38 (Year: 2010).*
Singh, P., et al., "Gold Nanoparticles in Diagnostics and Therapeutics for Human Cancer", Int. J. Mol. Sci., pp. 1-16 (Year: 2018).*

(Continued)

Primary Examiner — Michael G. Hartley
Assistant Examiner — Lance W Rider
(74) Attorney, Agent, or Firm — Saliwanchik, Lloyd & Eisenschenk

(57) ABSTRACT

The present invention relates to novel nanoparticles which can be advantageously used in the health sector as diagnostic and/or therapeutic agents. Nanoparticles of the invention comprise a metallic material at least partly covered with a hafnium oxide material or embedded therein. When compared to existing products, these nanoparticles offer a remarkable benefit over risk ratio. Specifically, these nanoparticles potentiate the efficiency of known metallic nanoparticles. Indeed, they retain the metal's intrinsic properties and are now in addition safely usable in a mammal, in particular in a human being. The invention also relates to methods for producing said nanoparticles, to compositions containing same, and to uses thereof.

9 Claims, 8 Drawing Sheets

(56) References Cited

U.S. PATENT DOCUMENTS

| | | | |
|---|---|---|---|
| 2004/0242953 A1* | 12/2004 | Good | A61K 51/1241 600/7 |
| 2005/0084869 A1 | 4/2005 | Kim | |
| 2005/0087719 A1 | 4/2005 | Gansau et al. | |
| 2005/0256360 A1* | 11/2005 | Hainfeld | A61K 41/0038 600/1 |
| 2005/0260137 A1 | 11/2005 | Acar et al. | |
| 2006/0099145 A1 | 5/2006 | Takeyama | |
| 2007/0031337 A1 | 2/2007 | Schulte | |
| 2007/0098642 A1 | 5/2007 | Bonitatebus, Jr. et al. | |
| 2007/0110816 A1* | 5/2007 | Jun | B82Y 30/00 424/490 |
| 2007/0197904 A1 | 8/2007 | Viglianti et al. | |
| 2007/0217996 A1 | 9/2007 | Levy et al. | |
| 2008/0003183 A1* | 1/2008 | Guo | A61K 41/0038 424/9.42 |
| 2009/0004258 A1 | 1/2009 | Yang et al. | |
| 2009/0304587 A1 | 12/2009 | Rubinstein et al. | |
| 2010/0040555 A1 | 2/2010 | Levy et al. | |
| 2011/0027375 A1 | 2/2011 | Tillement et al. | |
| 2011/0213192 A1 | 9/2011 | Levy et al. | |
| 2011/0223255 A1 | 9/2011 | Thiesen et al. | |
| 2012/0176016 A1* | 7/2012 | Bonitatibus, Jr. | B22F 1/02 313/46 |
| 2012/0203050 A1 | 8/2012 | Levy et al. | |
| 2014/0056813 A1 | 2/2014 | Pottier et al. | |
| 2014/0219926 A1 | 8/2014 | Cunkelman et al. | |
| 2014/0227343 A1 | 8/2014 | Pottier et al. | |
| 2014/0335015 A1 | 11/2014 | Pottier et al. | |
| 2015/0374818 A1 | 12/2015 | Borghi et al. | |
| 2016/0038616 A1 | 2/2016 | Pottier et al. | |
| 2016/0136303 A1 | 5/2016 | Poul et al. | |
| 2016/0136304 A1 | 5/2016 | Poul et al. | |
| 2016/0184225 A1 | 6/2016 | Pottier et al. | |
| 2016/0310614 A1 | 10/2016 | Pottier et al. | |

FOREIGN PATENT DOCUMENTS

| | | | |
|---|---|---|---|
| EP | 2 000 150 | 12/2008 | |
| EP | 2067485 | 6/2009 | |
| EP | 2 130 553 | 12/2009 | |
| EP | 2 305 310 | 4/2011 | |
| EP | 2 537 530 | 12/2012 | |
| FR | 2 922 106 | 4/2009 | |
| GB | 2415374 | 12/2005 | |
| JP | H05209072 A * | 1/1992 | |
| JP | 2001-527534 | 12/2001 | |
| JP | 2003-522149 | 7/2003 | |
| JP | 2005-273011 | 10/2005 | |
| JP | 2009-067613 | 4/2009 | |
| WO | WO 1993/26019 | 12/1993 | |
| WO | WO 2001/58458 | 8/2001 | |
| WO | WO 01/37721 A2 | 5/2003 | |
| WO | WO 03/035113 | 5/2003 | |
| WO | WO 03/075961 | 9/2003 | |
| WO | WO 05/046733 | 5/2005 | |
| WO | WO 2005/063305 | 7/2005 | |
| WO | WO 2005/120590 | 12/2005 | |
| WO | WO 2006/051732 | 5/2006 | |
| WO | WO 2006/138268 | 12/2006 | |
| WO | WO 2007/116954 | 10/2007 | |
| WO | WO 2008/007290 | 1/2008 | |
| WO | WO 2008/033031 | 3/2008 | |
| WO | WO 2008/035985 | 3/2008 | |
| WO | WO 2008/059419 | 5/2008 | |
| WO | WO-2008059419 A1 * | 5/2008 | A61K 41/0038 |
| WO | WO 2009/081287 | 7/2009 | |
| WO | WO 2009/142754 | 11/2009 | |
| WO | WO 2009/147214 | 12/2009 | |
| WO | WO 2010/048623 | 4/2010 | |
| WO | WO 2011/003999 | 1/2011 | |
| WO | WO 2011/070324 | 6/2011 | |
| WO | WO 2011/151631 | 12/2011 | |
| WO | WO 2012/104275 | 8/2012 | |
| WO | WO 2012/104277 | 8/2012 | |
| WO | WO 2013/087920 | 6/2013 | |

OTHER PUBLICATIONS

JPH05209072A Translation; accessed from: "https://patents.google.conn/patent/JPH05209072A/en?q=%22hafnium%22&q=radiotherapy&q=%22oxide+surface%22&oq=%22hafnium%22+radiotherapy+%22oxide+surface%22&page=1"; accessed on Jan. 2, 2019; pp. 1-10 (Year: 2019).*

Jie, N., et al., "Morphology in-Design Deposition of HfO2 Thin Films", J. Am. Ceram. Soc., pp. 3548-3460 (Year: 2008).*

Nanobiotix: "Release / Nanobiotix Starts Clinical Trial with Lead Product NBTXR3", Sep. 13, 2011, XP-002671267, Retrieved from Internet: URL:http://www.nanobiotix.com/news/release/nanobiotix-starts-clinical-trial-with-lead-product-nbtxr3/, retrieved on Mar. 12, 2012, pp. 1-2.

Sargentis, C. et al "Simple method for the fabrication of a high dielectric constant metal-oxide-semiconductor capacitor embedded with Pt nanoparticles" *Applied Physics Letters*, Feb. 15, 2006, pp. 73106-1-73106-3, vol. 88, No. 7.

Written Opinion in International Application No. PCT/EP2012/075731, dated Jan. 28, 2013, pp. 1-6.

Maggiorella, L., et al., "Nanoscale radiotherapy with hafnium oxide nanoparticles," *Future Oncology*, 2012, vol. 8, No. 9, pp. 1167-1181.

Shevchenko, E.V., et al., "Gold/Iron Oxide Core/Hollow-Shell Nanoparticles," *Advanced Materials*, 2008, vol. 20, pp. 4323-4329.

Chen, Y. et al. "Nano neodymium oxide induces massive vacuolization and autophagic cell death in non-small cell lung cancer NCI-H460 cells" *Biochemical and Biophysical Research Communications*, 2005, pp. 52-60, vol. 337, XP-002495930.

Fortin, M.-A. et al. "Polyethylene glycol-covered ultra-small $Gd_2O_3$ nanoparticles for positive contrast 1.5 T magnetic resonance clinical scanning" *Nanotechnology*, 2007, pp. 1-9, vol. 18, XP-002495929.

Smith, B. W. et al. "Rhenium oxide nanoparticles for the targeted radiotherapy of solid tumors" *Abstracts of Papers American Chemical Society*, Aug. 2004, p. U6, vol. 228, Part 2, XP-008096435.

Tsai, Y. et al. "Novel synthesis of cerium oxide nanoparticles for free radical scavenging" *Nanomedicine*, 2007, pp. 325-332, vol. 2, No. 3, XP-008096453.

Webb, P. A. "Volume and Density Determinations for Particle Technologists" Retrieved from the Internet: URL: http://www.micromeritics.com/pdf/app_articles/density_determinations.pdf>, Feb. 2001, pp. 1-16, XP-002495931.

Written Opinion in International Application No. PCT/EP2009/056880, dated Dec. 7, 2009, pp. 1-8.

Petri-Fink, A. et al. "Development of functionalized superparamagnetic iron oxide nanoparticles for interaction with human cancer cells" *Biomaterials*, May 2005, pp. 2685-2694, vol. 26, No. 15.

Jain, T. K. et al. "Iron Oxide Nanoparticles for Sustained Delivery of Anticancer Agents" *Molecular Pharmaceutics*, May-Jun. 2005, pp. 194-205, vol. 2, No. 3.

Johannsen, M. etal. "Evaluation of magnetic fluid hyperthermia in a standard rat model of prostate cancer" *J. Endourol.*, 2004, pp. 495-500, vol. 18.

Chouly, C. et al. "Development of superparamagnetic nanoparticles for MRI: effect of particle size, charge and surface nature on biodistribution." *J. Microencapsul.*, 1996, pp. 245-255, vol. 13.

Roy, I. et al. "Ceramic-based nanoparticles entrapping water-insoluble photosensitizing anticancer drugs: a novel drug-carrier system for photodynamic therapy." *J. Am. Chem. Soc.*, 2003, pp. 7860-7865, vol. 125.

Bergey, E. J. et al. "DC magnetic field induced magnetocytolysis of cancer cells targeted by LH-RH magnetic nanoparticles in vitro." *Biomed. Microdevices*, 2002, pp. 293-299, vol. 4.

Entry for "ferromagnetic". Dictionary.com online dictionary. <http://dictionary.reference.com/browse/ferromagnetic>. Accessed Mar. 5, 2012.

(56) References Cited

OTHER PUBLICATIONS

"Selected ferrites," in CRC Handbook of Chemistry and Physics, 92nd Edition (Internet version 2012), W.M. Haynes, ed., CRC Press/Taylor and Francis, Boca Raton, FL. p. 12-114.
Liu, X. M. et al. "Synthesis of maghemite sub-microspheres by simple solvothermal reduction method" *J. Solid State Chem.* 2006, pp. 1554-1558, vol. 179, Available online Mar. 10, 2006.
Brun, E. et al. "Parameters governing gold nanoparticle X-ray radiosensitization of DNA in solution" *Colloids and Surfaces B: Biointerfaces*, 2009, pp. 128-134, vol. 72, No. 1.
Zhang, S. X. et al. "Quantifying tumor-selective radiation dose enhancements using gold nanoparticles: a monte carlo simulation study" *Biomedical Microdevices*, 2009, pp. 925-933, vol. 11, No. 4.
Written Opinion in International Application No. PCT/EP2010/059871, dated Aug. 5, 2010, pp. 1-7.
Hoopes, P. J. et al. "Assessment of intratumor non-antibody directed iron oxide nanoparticle hyperthermia cancer therapy and antibody directed IONP uptake in murine and human cells" *Proc SPIE Int Soc Opt Eng.*, Feb. 23, 2009, pp. 1-17.
Chithrani, B. D. et al. "Determining the Size and Shape Dependence of Gold Nanoparticle Uptake into Mammalian Cells" *Nano Letters*, 2006, pp. 662-668, vol. 6. No. 4.
Hofmann-Amtenbrink, M. et al. "Superparamagnetic nanoparticles for biomedical applications" *Nanostructured Materials for Biomedical Applications*, 2009, 119-149.
Jong, W. et al. "Drug delivery and nanoparticles:Applications and hazards" *International Journal of Nanmedicine*, 2008, pp. 133-149, vol. 3, No. 2.
Mahmoudi, M. et al. "Superparamagnetic iron oxide nanoparticles (SPIONs): Development, surface modification and applications in chemotherapy" *Advanced Drug Delivery Reviews*, 2011, pp. 24-46, vol. 63.
Bakandritsos, A. et al. "Synthesis and Characterization of Iron Oxide Nanoparticles Encapsulated in Lipid Membranes" *Journal of Biomedical Nanotechnology*, 2008, pp. 313-318, vol. 4.
Fortin-Ripoche, J.-P. et al. "Magnetic Targeting of Magnetoliposomes to Solid Tumors with MR Imaging Monitoring in Mice: Feasibility" *Radiology*, May 2006, pp. 415-424, vol. 239, No. 2.
Written Opinion in International Application No. PCT/EP2012/051507, dated Sep. 11, 2012, pp. 1-7.
Aime, S. et al. "Gd-Loaded Liposomes as $T_1$, Susceptibility, and CEST Agents, All in One" *Journal of the American Chemical Society*, 2007, pp. 2430-2431, vol. 129, No. 9.
Arruebo, M. et al. "Magnetic nanoparticles for drug delivery" *Nano Today*, Jun. 2007, pp. 22-32, vol. 2, No. 3.
Written Opinion in International Application No. PCT/EP2012/051510, dated Aug. 30, 2012, pp. 1-8.
Golovko, D. et al. "Accelerated stem cell labeling with ferucarbotran and protamine" *European Journal of Radiology*, 2010, pp. 640-648, vol. 20.
Sun, Y. et al. "An improved way to prepare superparamagnetic magnetite-silica core-shell nanoparticles for possible biological application" *Journal of Magnetism and Magnetic Materials*, 2005, pp. 65-70, vol. 285.
Database EMBASE Accession No. 0018572655, Hodenius, M.A.J. et al. "Synthesis, physicochemical characterization and MR relaxometry of aqueous ferrofluids" *Journal of Nanoscience and Nanotechnology*, May 2008, p. 1.
Honda, H. et al. "Study of hyperthermia for cancer using a magnetic liposome particles" *Banyu Life Science Foundation International Drug Discovery Engineering Symposium*, 2005, pp. 29-33, vol. 5.
Toagosei Group, Research Annual Report, Jan. 1, 2011, pp. 27-30, vol. 14.
McCarthy, J. et al. "Multifunctional magnetic nanoparticles for targeted imaging and therapy" *Advanced Drug Delivery Reviews*, 2008, pp. 1241-1251, vol. 60.
Lorenzato, C. et al. "MRI contrast variation of thermosensitive magnetoliposomes triggered by focused ultrasound: a tool for image-guided local drug delivery" *Contrast Media Mol. Imaging*, 2013, pp. 185-192, vol. 8.

Taglienti, A., et al., "Kinetics of drug release from a hyaluronan-steroid conjugate investigated by Nmr spectroscopy," *Carbohydrate Research*, 2009, vol. 344, pp. 245-249.
Motosugi, U. et al. "II The Latest Trend of MRI Contrast Agent, Emergence of liver-specific contrast agent for possible bolus injection, 1. SPIO Formulation" *Innervision*, (17-9), 2002, pp. 23-25.
Radu, M. et al. "Exposure to Iron Oxide Nanoparticles Coated with Phospholipid-Based Polymeric Micelles Induces Biochemical and Histopathological Pulmonary Changes in Mice" *International Journal of Molecular Sciences*, 2015, pp. 29417-29435, vol. 16.
Salomir, R. et al. "Local Delivery of Magnetic Resonance (MR) Contrast Agent in Kidney Using Thermosensitive Liposomes and MR Imaging•Guided Local Byperthermia: A Feasibility Study In Vivo" *Journal of Magnetic Resonance Imaging*, 2005, pp. 534-540, vol. 22.
Kato, Y. et al. "Monitoring of Release of Cargo :From Nanocarriers by MRI/MR Spectroscopy (MRS): Significance of $T_2/T^*_2$ Effect of Iron Particles" *Magnetic Resonance in Medicine*, 2009, pp. 1059-1065, vol. 61.
Herrera, A., et al., "Breakthrough concept in local treatment for advanced tumors," NTBX Chicago, Jun. 3, 2013, pp. 1-51.
Pottier, A., et al., "New Use of Metals as Nanosized Radioenhancers," *Anticancer Research*, Jan. 2014, vol. 34, No. 1, pp. 443-453.
Written Opinion in International Application No. PCT/EP2014/051367, dated May 20, 2014, pp. 18.
Bowen, P., "Particle Size Distribution Measurement from Millimeters to Nanometers and from Rods to Platelets," *Journal of Dispersion Science and Technology*, Jan. 1, 2002, vol. 23, No. 5, pp. 631-662.
Written Opinion in International Application No. PCT/EP2014/061296, dated Sep. 5, 2014, pp. 1-9.
Yu, S. et al. "Carboxyl group (-$CO_2H$) functionalized ferrimagnetic iron oxide nanoparticles for potential bio-applications" *Journal of Materials Chemistry*, 2004, pp. 2781-2786, vol. 14.
Ismail, M.F. et al. "Potential therapeutic effect of nanobased formulation of rivastigmine on rat model of Alzheimer's disease" *International Journal of Nanomedicine*, 2013, pp. 393-406, vol. 8.
Written Opinion in International Application No. PCT/EP2014/062947, dated Jul. 21, 2014, pp. 14.
Ahmad, M. et al. "Synthesis of Silver Nanoparticles in Chitosan, Gelatin and Chitosan/Gelatin Bionanocomposites by a Chemical Reducing Agent and Their Characterization" *Molecules*, 2011, pp. 7237-7248, vol. 16.
U.S. Appl. No. 61/759,852, filed Feb. 1, 2013.
Guo, Z.X., et al., "Generation of alginate gel particles with AuNPs layers by polydimethylsiloxane template," *Biomicrofluidics*, Jan. 1, 2011, vol. 5, No. 2, pp. 026502-026502-6.
Ikegami, S., et al., "Effect of Viscous Indigestible Polysaccharides on Pancreatic-Biliary Secretion and Digestive Organs in Rats," *Journal of Nutrition*, Jan. 1, 1990, vol. 120, No. 4, pp. 353-360.
Witteveen, J.A., et al., "Gelatin/glycerol coating to preserve mechanically compliant nanowire electrodes from damage during brain implantation," *Journal of Vacuum Science & Technology B*, Nov./Dec. 2010, vol. 28, No. 6, pp. C6K13-C6K16.
Written Opinion in International Application No. PCT/EP2014/062976, dated Aug. 28, 2014, pp. 1-5.
DeKrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.
Written Opinion in International Application No. PCT/EP2014/078619, dated Mar. 26, 2015, pp. 1-6.
Pernodet, N. et al. "Adverse Effects of Citrate/Gold Nanoparticles on Human Dermal Fibroblasts" *Small*, 2006, pp. 766-773, vol. 2, No. 6.
Newkirk, CE. et al. "Comparative study of hematological responses to platinum group metals, antimony and silver nanoparticles in animal models" *J Environ Sci Health A Tox Hazard Subst Environ Eng*, 2014, pp. 269-280, vol. 49, No. 3. Abstract only.
Noel, C. et al. "Gold nanoparticles induce apoptosis, endoplasmic reticulum stress events and cleavage of cytoskeletal proteins in human neutrophils" *Toxicol In Vitro*, Mar. 2016, pp. 12-22, vol. 31.

(56) References Cited

OTHER PUBLICATIONS

Lee, U. et al. "Cytotoxicity of gold nanoparticles in human neural precursor cells and rat cerebral cortex" *Journal of Bioscience Bioengineering*, Mar. 2016, pp. 341-344, vol. 121, No. 3.

Li, C.-H. et al. "Gold Nanoparticles Increase Endothelial Paracellular Permeability by Altering Components of Endothelial Tight Junctions, and Increase Blood-Brain Barrier Permeability in Mice" *Toxicological Sciences*, Nov. 2015, pp. 192-203, vol. 148, No. 1.

Dahal, N. "Synthesis and Characterizations of Novel Magnetic and Plasmonic Nanoparticles", An Abstract of a Dissertation, 2010, pp. 1-175.

Schuemann, J. et al. "Roadmap to clinical use of gold nanoparticles for radiosensitization" *Int J Radiat Oncol Biol Phys.*, Jan. 1, 2016, pp. 1-33, vol. 94, No. 1.

Nanobiotix: "Nanobiotix presents successful Phase I results for its lead nanomedicine product NBTXR3 at ASCO", Jun. 2, 2014, pp. 1-6.

Nanobiotix: "Nanobiotix reports positive preliminary results in Head and Neck cancer Phase I/II clinical trial with NBTXR3", Jun. 9, 2015, pp. 1-5.

Roeske, J. C. et al. "Characterization of the Theorectical Radiation Dose Enhancement from Nanoparticles" *Technology in Cancer Research and Treatment*, Oct. 2007, pp. 395-401, vol. 6, No. 5.

Schlathölter, T. et al. "Improving proton therapy by metal-containing nanoparticles: nanoscale insights" *International Journal of Nanomedicine*, 2016, pp. 1549-1556, vol. 11.

\* cited by examiner

C

Reference:

Gold nanoparticles from example 1:

Reference: gold nanoparticles with CFC structure to determine Lλ:

| | Diameter (cm) | $d_{hkl}$ (Å) | | Lλ |
|---|---|---|---|---|
| D1 | 2,5 | $d_{111}$ | 2,354 | 2,982 |
| D2 | 2,9 | $d_{200}$ | 2,039 | 2,991 |
| D3 | 4,1 | $d_{220}$ | 1,442 | 2,980 |
| D4 | 4,8 | $d_{311}$ | 1,229 | 2,949 |
| | | | | 2,975 |

Indexation for gold nanoparticles from example 1:

| | Diameter (cm) | Lλ | $d_{hkl}$ (Å) | Attribution |
|---|---|---|---|---|
| D1 | 2,6 | 2,975 | 2,266 | $d_{111}$ |
| D2 | 2,9 | 2,975 | 2,035 | $d_{200}$ |
| D3 | 4,3 | 2,975 | 1,399 | $d_{220}$ |
| D4 | 4,7 | 2,975 | 1,279 | $d_{311}$ |
| | | | | Gold CFC structure |

FIGURE 4B

Indexation for gold@HfO$_2$ nanoparticles from example 4:

| Diameter (cm) | | Experimental d$_{hkl}$ (Å) | d$_{hkl}$ (Au) | Attribution (Au) | d$_{hkl}$ (HfO$_2$) | Attribution (HfO$_2$) |
|---|---|---|---|---|---|---|
| D1 | 2,1 | 2,798 | | | 2,820 | d$_{111}$ |
| D2 | 2,5 | 2,356 | 2,354 | d$_{111}$ | | |
| D3 | 2,9 | 2,035 | 2,039 | d$_{200}$ | | |
| D4 | 3,7 | 1,599 | | | 1,600 | d$_{-311}$ |
| D5 | 4,3 | 1,399 | 1,442 | d$_{220}$ | 1,410 | d$_{-321}$ |
| D6 | 4,5 | 1,316 | | | 1,318 | d$_{-223}$ |
| D7 | 4,9 | 1,226 | 1,229 | d$_{311}$ | 1,237 | d$_{-411}$ |
| | | | Gold CFC structure | | | Hafnium oxide Monoclinic structure |

NANOPARTICLES COMPRISING METALLIC AND HAFNIUM OXIDE MATERIALS, PREPARATION AND USES THEREOF

CROSS-REFERENCE TO RELATED APPLICATIONS

This application is the U.S. national stage application of International Patent Application No. PCT/EP2012/075731, filed Dec. 17, 2012, which claims benefit of provisional U.S. Patent Application Ser. No. 61/576,437, filed Dec. 16, 2011.

The present invention relates to novel nanoparticles which can be advantageously used in the health sector as diagnostic and/or therapeutic agents. Nanoparticles of the invention comprise a metallic material at least partly covered with an oxide material, preferably an hafnium oxide material, or embedded therein. When compared to existing products, these nanoparticles offer a remarkable benefit over risk ratio. Specifically, these nanoparticles potentiate the efficiency of known metallic nanoparticles. Indeed, they retain the metal's intrinsic properties and are now in addition safely usable in a mammal, in particular in a human being. The invention also relates to methods for producing said nanoparticles, compositions containing same, and uses thereof.

BACKGROUND

Nanotechnology offers revolutionary strategies to improve healthcare. However, as for any healthcare product, in the field of nanomedicine, the concept of expected/unexpected toxicity should be considered, from the perspective of both what might be anticipated from the chemical and pharmacological properties of a medicinal product, and the knowledge in terms of previous observation or documentation.

The nanoparticles' toxicological issues are of most importance when designing a nanomaterial. The potential toxicity of engineered nanomaterials developed for diagnostic or therapeutic applications is to be considered and encompasses phenomena such as release of toxic species into biological media, redox phenomena, electron transfer and reactive oxygen species (ROS) production. Also, adsorption of proteins on the nanoparticles' surfaces may trigger various adverse phenomena such as change in protein conformation and subsequent loss of enzyme activity, fibrillation, or exposure to new antigenic epitopes. Pharmacokinetics is a determinant parameter of efficacy and safety prediction. Nanoparticles which are not or only poorly degraded after being captured by mononuclear phagocytic cells can be entrapped in the reticuloendothelial system (RES), where they accumulate and can induce undesirable side effects.

Nanoparticle surface coating (functionalization) is perceived as an attractive approach to improving nanoparticles' safety by playing different roles such as preventing nanoparticle bioreactivity and nanoparticle dissolution. Indeed, the coating of nanoparticles with a protective shell appears as an effective means of reducing their toxicity. Suitable shell materials include biocompatible organic or inorganic substances such as polyethyleneglycol compounds (PEG compounds), silica ($SiO_2$) and biocompatible polymers. However, these coatings are environmentally labile or degradable and an initially non-toxic material may become hazardous after shedding its coat, when the core of the nanoparticle is exposed to the body.

Cancer is a leading cause of death worldwide, accounted for 7.6 million deaths (around 13% of all deaths) in 2008. Deaths from cancer are projected to continue rising, with an estimated 12 million deaths in 2030 (WHO). Surgery, radiotherapy, and pharmaceuticals are of central importance as anti-cancer treatment modalities; each of them can be used alone or in combination, depending on the type of cancer being treated. The choice of the therapy depends on the location and grade classification of the tumor and the stage of the disease, as well as the health state of the patient.

Anticancer agents that target the cell cycle and the DNA, such as cytotoxics or X-rays, are among the most effective in clinical use and have produced a significant increase in the survival of patients with cancer when used alone or in combination with drugs that have different mechanisms of action. They are also extremely toxic and show a narrow therapeutic window.

Therefore, there is still considerable excitement in the cancer field to modify the therapeutic ratio, aiming at efficacy and safety improvements.

Nanotechnology offers an advantageous solution to deliver therapies directly and selectively to cancerous cells. In recent years, metallic nanoparticles have shown great promise for diagnostic and therapy. Among metal nanoparticles, gold nanoparticles have been in particular proposed, especially as radiosensitizers in the context of radiotherapy (WO2004/112590), contrast agents in the context of diagnostic (WO2003/075961), photothermal agents in the context of hyperthermia therapy (WO2009/091597), and drug carriers in the context of chemotherapy (WO2002/087509).

Gold has long been and is still considered as bioinert (i.e., lack of biochemical reactivity) and thus usable in vivo in a mammal (WO2011/127061). This opinion however is now considered doubtful by the inventors and by others.

Recent papers have questioned the inert behavior of gold nanoparticles in biological media that could reduce their use in medical applications.

Cho, W. S. et al. (Acute toxicity and pharmacokinetics of 13 nm sized PEG-coated gold nanoparticles, Toxicology and Applied Pharmacology 236 (2009) 16-24) have carried out an in vivo toxicity study using 13 nm-size gold nanoparticles coated with PEG. The PEG-5000-coated gold 13 nm nanoparticles were injected intravenously (0, 0.17, 0.85 or 4.26 mg/Kg of body weight in BALB/C mice). The nanoparticles were found to accumulate in the liver and spleen for up to 7 days. In addition, Transmission Electron Microscopy (TEM) images showed that numerous cytoplasmic vesicles and lysosomes of liver Kupffer cells and spleen macrophages contained PEG-coated gold nanoparticles. 7 days post-treatment, apoptosis of liver hepatocytes was significantly higher for mice given 0.85 and 4.26 mg/Kg of gold nanoparticles. Apoptotic cells was about 10% in the high dose group at seven day. Although the transient inflammatory responses were negligible for the toxicity of 13 nm PEG-coated gold nanoparticles, apoptosis of liver hepatocytes is an important adverse effect induced by treatment of 13 nm PEG-coated gold nanoparticles.

Sadauskas, E. et al. (Protracted elimination of gold nanoparticles from mouse liver, Nanomedicine 5 (2009) 162-9) studied the fate of 40 nm gold nanoparticles after intravenous injections. Gold nanoparticles were injected intravenously (0.5 mL–9×10$^{10}$ particles per mL) into adult female C57BL mice. Experimental groups were killed after 1 day, 1 month, 3 months and 6 months. The control group was killed after 1 day. The ICP-MS finding of a 9% fall in the content of gold from day 1 to 6 months revealed a protracted turnover of gold-loaded Kupffer cells. Autometallographic (AMG) staining showed that there was a decreasing number of Kupffer cells containing gold nanoparticles after a long exposure period and a significant decrease in the AMGstained areas after 1 month. The authors believe that this reflects cannibalism between Kupffer cells. They observed unhealthy-looking large gold-containing lysosomes in animals that had survived for 3 to 6 months, which may support the notion of Kupffer cells dying and being phagocytosed by surrounding Kupffer cells.

Chen, Y. S. et al. (Assessment of the in vivo toxicity of gold nanoparticles, Nanoscale Res. Lett. 4(8) (2009) 858-64) have carried out an in vivo toxicity study using 3, 5, 12, 17, 37, 50 and 100-nm gold nanoparticles. The gold nanoparticles were injected intraperitoneally into BALB/C mice at dose of 8 mg/Kg/week. Gold nanoparticles ranging from 8 to 37 nm in size induced severe sickness in mice (median survival time=21 days). Pathological examination of the major organs of the mice in the diseased groups indicated an increase of Kupffer cells in the liver (activation of Kupffer cells suggested toxic potential for gold nanoparticles in this zone), loss of structural integrity in the lungs (structures observed similar to that of emphysema) and diffusion of white pulp in the spleen. The pathological abnormality was associated with the presence of gold nanoparticles at the diseased sites.

The inventors surprisingly discovered and now herein describe that hafnium oxide is able, when properly used in combination with metallic material, to render said metallic material, in particular gold, non-toxic, without being detrimental to the metal's therapeutic and diagnostic properties, thereby rendering the product of the invention advantageously usable in vivo in a mammal.

The inventors further believe that the claimed combination of metallic and hafnium oxide materials may be responsible for an efficient deposit of energy within the tumor structure, said deposit being responsible for the dramatic enhancement of tumor destruction in vivo when activated by radiation when compared to standard treatments.

SUMMARY OF THE INVENTION

The inventors herein provide a nanoparticle comprising a metallic material at least partly covered with a hafnium oxide material or embedded therein. In a particular embodiment, the nanoparticle of the invention is a core-shell metal-oxide nanoparticle which comprises a metallic material fully covered with a hafnium oxide material or embedded therein. They also provide a composition comprising such a nanoparticle together with a pharmaceutically acceptable carrier. This composition may be a diagnostic composition or a pharmaceutical composition. The inventors further describe their products for use in a mammal, preferably in a human being, as a diagnostic agent and/or as a therapeutic agent, in particular in oncology, more particularly when the nanoparticle is exposed to radiation.

BRIEF DESCRIPTION OF THE FIGURES

FIG. 1A provides an illustration of a metallic crystallite or an aggregate of metallic crystallites.

FIG. 1B provides an illustration of core-shell metal-oxide nanoparticles which comprise a metallic material fully covered with a hafnium oxide material or embedded therein.

FIG. 1C provides an illustration of nanoparticles comprising a metallic material at least partly covered with a hafnium oxide material or embedded therein.

FIGS. 4A-4B: The crystalline structure of the as-prepared gold nanoparticles (example 1) is determined by electronic diffraction.

FIG. 4A shows the electronic diffraction pattern of reference nanoparticles (gold nanoparticles with Cubic Face Center structure are used as a reference to establish the camera constant (Lλ) of the transmission electronic microscope) and of gold nanoparticles (GNPs) from example 1.

FIG. 4B reports the indexation of the gold nanoparticles from example 1, electronic diffraction pattern showing a Cubic Face Center (CFC) structure of the gold nanoparticles.

Indexing the electronic diffraction pattern consists of the following steps:
1) Establishing the camera constant from the electronic diffraction pattern of the reference,
2) Measuring the ring diameter (D1, D2, . . . , Dn) of the electronic diffraction pattern of the gold nanoparticles from example 1,
3) Calculating the $d_{hkl}$, using the expression $d_{hkl}=L*\lambda/(Dn/2)$,
4) Using existing structure database to index each ring.

Figures 5A, 5B:
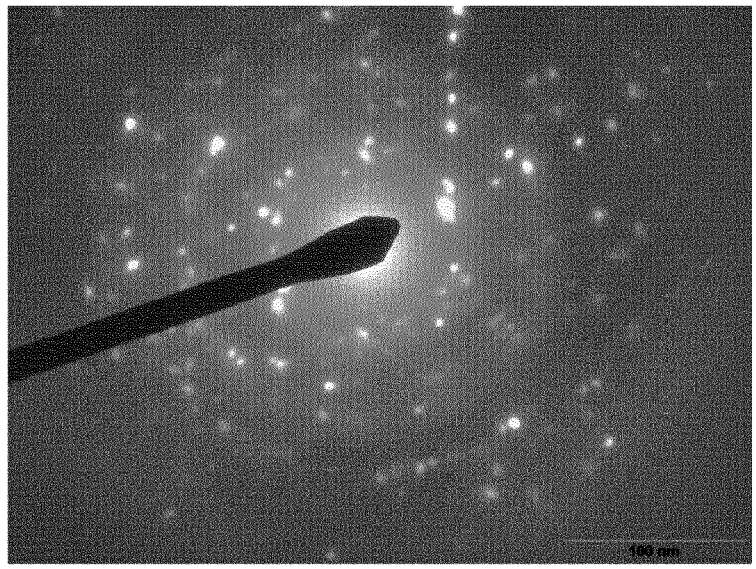

FIGS. 5A-5B provide pictures of the electronic diffraction pattern of core@shell Au@HfO$_2$ type assembly of a gold nanoparticle and hafnium oxide material from example 4.

FIG. 5A shows the electronic diffraction pattern of gold@HfO$_2$ nanoparticles from example 4.

FIG. 5B reports the indexation of the gold@HfO$_2$ nanoparticles (from example 4).

Figure 4A:
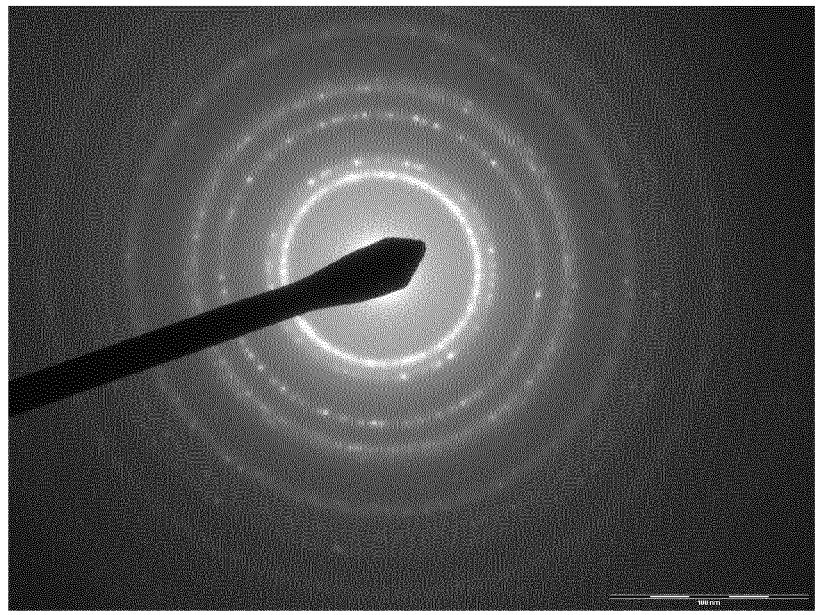

Indexing the electronic diffraction pattern consists of the following steps:
1) Establishing the camera constant from the electronic diffraction pattern of the reference (FIG. 4A),
2) Measuring the ring diameter (D1, D2, Dn) of the electronic diffraction pattern of the Au@HfO$_2$ nanoparticles from example 4,
3) Calculating the $d_{hkl}$, using the expression $d_{hkl}=L*\lambda/(Dn/2)$, and
4) Using existing structure database to index each ring.

Figure 6:
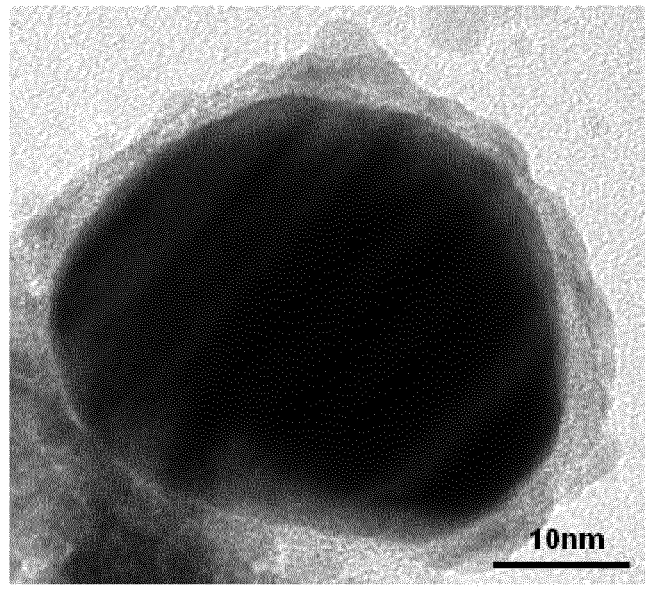

FIG. 6 provides a transmission electron microscopy picture of a core@shell Au@HfO$_2$ type assembly of gold nanoparticles and hafnium oxide material from example 4. On this cliché, it can be observed that a shell covers the gold nanoparticle surface. This shell comprises hafnium oxide material, as demonstrated by electronic diffraction.

DETAILED DESCRIPTION

The nanoparticle of the invention comprises a metallic material at least partly covered with a hafnium oxide material or embedded therein.

In the context of metal-oxide semiconductor (MOS) development for miniaturization of transistors for electronic devices, Sargentis, C. et al. (Simple method for the fabrication of a high dielectric constant metal-oxide-semiconductor capacitor embedded with Pt nanoparticles, Appl. Phys. Lett. 88(073106) (2006) 1-3) developed a simple electron evaporation method to fabricate a MOS device embedded with Pt nanoparticles on its SiO$_2$/HfO$_2$ interface. The fabricated Pt nanoparticles have an average diameter of 4.9 nm and the sheet density is of $3.2\times10^{12}$ nanoparticles/cm$^2$. This object, intended for use in the development of electronic devices, is composed of metallic nanoparticles partially embedded in a hafnium oxide layer. This object is a sheet and not a nanoparticle, contrary to the object of the invention.

In a particular embodiment, the nanoparticle of the invention is a core-shell metal-oxide nanoparticle which comprises a metallic material fully covered with a hafnium oxide material or embedded therein.

In the spirit of the invention, the term "nanoparticle" refers, as further explained below, to products, in particular synthetic products, with a size in the nanometer range, typically between 1 nm and 500 nm.

The metallic material is typically a metallic crystallite or an aggregate of metallic crystallites.

The nanoparticle of the invention advantageously comprises one or several metallic crystallites.

In a preferred embodiment, the nanoparticle of the invention comprises several hafnium oxide crystallites and/or several hafnium oxide crystallite aggregates.

In a particular embodiment, each of the metallic material and the hafnium oxide material consists of a crystallite or an aggregate of crystallites.

In another particular embodiment, the nanoparticle of the invention is a core-shell metal oxide nanoparticle comprising a metallic material which is typically a metallic crystallite or an aggregate of metallic crystallites fully covered with a hafnium oxide material.

The term "crystallite" herein refers to a crystalline product. The size of the crystallite and its structure and composition may be analyzed from an X-ray diffractogram.

The term "aggregate of crystallites" refers to an assemblage of crystallites strongly, typically covalently, bound to each other.

The metallic material can advantageously be selected from gold (Au), silver (Ag), platinum (Pt), palladium (Pd), tin (Sn), tantalum (Ta), ytterbium (Yb), zirconium (Zr), hafnium (Hf), terbium (Tb), thulium (Tm), cerium (Ce), dysprosium (Dy), erbium (Er), europium (Eu), holmium (Ho), iron (Fe), lanthanum (La), neodymium (Nd), praseodymium (Pr), lutetium (Lu) and mixtures thereof. The metal is preferably selected from gold, silver, tantalum, platinum, palladium, tin, zirconium, hafnium, lutetium and iron, even more preferably from zirconium, hafnium, tantalum and gold. Most preferably the metallic material is gold or tantalum, even more preferably gold.

In a particular embodiment, at least 80%, for example 85%, 86%, 87%, 88% or 89%, of the metallic material is protected from any interaction with a biological material by the hafnium oxide material. More preferably, at least 90%, typically between 90% and 98%, for example 95%, of the metallic material is protected from any interaction with a biological material by the hafnium oxide material.

In another particular embodiment, the nanoparticle of the invention is a core-shell metal-oxide, also identified as core@shell metal@oxide, nanoparticle which comprises a metallic material fully covered with an hafnium oxide material or embedded therein.

The nanoparticle of the invention comprises a metallic material which is either at least partially covered with a hafnium oxide material or fully covered with a hafnium oxide material, depending on the intended use.

For example, when the nanoparticles of the invention are used as contrast agents in the context of diagnostic or as radiosensitizers in the context of therapy, the metallic material is advantageously fully covered with a hafnium oxide material (core@shell metal@oxide nanoparticle), but when the nanoparticles of the invention are used as photothermal agents in the context of hyperthermia therapy or as drug carriers in the context of chemotherapy, the metallic material is preferably at least partly covered with a hafnium oxide material.

In a particular embodiment, in order to retain the intrinsic properties of metal materials, it may be desirable that the hafnium oxide material covering or embedding the metallic material allows the diffusion of small molecules. In particular it is important that the hafnium oxide material covering or embedding the metallic material allows the passage of water or drugs, but protects the metallic material from any interaction with biological materials.

In the context of diagnostic or radiotherapy, a full coverage of the metal composition is appreciable. In the context of diagnostic, this full coverage is even preferred to optimize safe use of the product.

The appropriate coverage of the metallic material by the hafnium oxide material may be adjusted so that the surface area of the nanoparticles, when determined by BET (Brunauer, Emmett and Teller) surface area analysis, is equal to or greater than the surface area of the nanoparticles when typically determined by the CTAB surface area analysis.

The BET surface area analysis is based on the absorption of a gas, usually nitrogen, on the surface of the nanoparticles (the nanoparticles are in the form of powder). The BET surface area provides the "total" surface of the nanoparticles, including porosity.

The CTAB surface area analysis is based on the absorption of the cetyltrimethylammonium bromide (CTAB) molecule on the surface of the nanoparticles (the nanoparticles are in solution). The CTAB molecule is relatively large so that it is not adsorbed in micropores. Thus, the CTAB surface area reflects only the surface of the nanoparticle that is available for interaction with large molecules, such as interactions with biological materials. Other molecules (such as proteins) could be used otherwise in the context of the invention to estimate this nanoparticle surface area.

When the nanoparticle comprises a metallic material fully covered with a hafnium oxide material, the BET surface area is correlated to the calculated surface, taking into account the shape of the nanoparticle and the relative proportion of metal and hafnium oxide materials constituting the nanoparticle, both being determined, typically by quantification of the metal and hafnium elements, using Inductively Coupled Plasma Mass Spectrometry (ICP MS) analysis.

The nanoparticle's shape can be, for example, round, flat, elongated, polygonal, spherical, ovoid or oval, and the like. The shape can be determined or controlled by the method of production and adapted by the person of the art.

As the shape of the particles can influence their biocompatibility, particles having a quite homogeneous shape are preferred. For pharmacokinetic reasons, nanoparticles being essentially spherical, round or ovoid in shape are thus preferred. Such a shape also favors the nanoparticles' interaction with or uptake by cells. A spherical or round shape is particularly preferred.

The terms "size of the nanoparticle" and "largest size of the nanoparticle" herein refer to the "largest dimension of the nanoparticle". Transmission Electron Microscopy (TEM) can be used to measure the size of the nanoparticle. As well, Dynamic Light Scattering (DLS) can be used to measure the hydrodynamic diameter of nanoparticles in solution. These two methods may further be used one after the other to compare size measurements and confirm said size.

Typically, the largest dimension is the diameter of a nanoparticle of round or spherical shape, or the longest length of a nanoparticle of ovoid or oval shape.

The largest dimension of a nanoparticle as herein defined is typically between about 10 nm and about 250 nm, preferably between about 20 nm and about 100 or about 200 nm, even more preferably between about 50 nm and about 150 nm.

The metallic crystallite size (largest dimension of a metallic crystallite) is typically between about 2 nm and about 100 nm, for example between about 2 nm and 60 nm or between about 10 nm and about 50 nm. Typical examples of metallic crystallite sizes are 5, 10, 15, 30 and 50 nm.

The metallic crystallite aggregate size (largest dimension of a metallic crystallite aggregate) is typically between about 20 nm and about 100 nm, for example between 20 nm and 50 nm.

The hafnium oxide crystallite size (largest dimension of a hafnium oxide crystallite) is typically between about 5 nm and about 50 nm, preferably between about 2 nm and about 50 nm, for example between 5 nm and 30 nm. Typical examples of hafnium oxide crystallite sizes are 2, 5, 10, 15, 20 and 25 nm.

The hafnium oxide crystallite aggregate size (largest dimension of a hafnium oxide crystallite aggregate) is typically between about 20 nm and about 100 nm, for example between 30 nm and 70 nm.

The hafnium oxide crystallite size or the hafnium oxide crystallite aggregate size corresponds, in the context of the core@shell metal@oxide nanoparticle, to the thickness of the hafnium oxide shell.

In the nanoparticle of the invention, the metallic material may be advantageously coated with an agent, herein defined as a "linker agent", favoring adhesion between the metal and the hafnium oxide material. Adhesion in the context of the present invention means that weak (hydrogen or electrostatic) or strong (covalent) interactions are established between the linker agent and the metal, and between the linker agent and the hafnium oxide material. Strong interactions are preferred. The linker agent is a compound capable of interacting, typically through covalent binding or electrostatic binding, with the metallic material's surface and with the hafnium oxide material.

The linker compound may comprise two terminal groups, $R_1$ and $R_2$. The function of $R_1$ is to interact with the metallic material and the function of $R_2$ is to interact with the hafnium oxide material.

$R_1$ may be selected for example from a carboxylate ($R_2$—X—COO$^-$), a phosphonic ($R_2$—X—PO(OH)$_2$), a phosphoric ($R_2$—X—O—PO(OH)$_2$), a phosphate ($R_2$—X—PO$_4^{3-}$) and a thiol ($R_2$—X—SH) group.

$R_2$ may be selected for example from a carboxylate ($R_1$—X—COO$^-$), a silane (($R_1$—X—Si(OR)$_3$) or (Si(OR)$_4$)), a phosphonic ($R_1$—X—PO(OH)$_2$), a phosphoric ($R_1$—X—O—PO(OH)$_2$), a phosphate ($R_1$—X—PO$_4^{3-}$) and a thiol ($R_1$—X—SH) group.

"X" is a chain which may be a linear or a cyclic chain containing at least one atom. The "X" chain may be selected for example from a chain containing carbon atoms (such as an alkane chain), a chain containing carbon and oxygen atoms (such as a polyethylene oxide chain or a carbohydrate chain), a chain containing silicon atoms (such as a silicon chain), and a chain containing phosphor atoms (such as a polyphosphate chain).

In a preferred embodiment, the metallic material and/or the hafnium oxide material of the claimed nanoparticles are bound to drug molecules.

Drug molecules may interact with either the metallic material and/or the hafnium oxide material via, for instance, hydrogen interactions, electrostatic interactions, or covalent bonding. The drug molecule may further comprise a cleavable linkage allowing the release of the drug molecule when the nanoparticle is exposed to a specific stimulus.

Such a cleavable linkage can be selected, for example, from a disulfide linkage or a pH-sensitive linkage such as a hydrazone linkage.

The specific stimulus capable of cleaving the linkage may be an environmental stimulus or a physical stimulus, typically an external physical stimulus. An environmental stimulus capable of cleaving the linkage may be, for example, the pH, capable of cleaving the pH-sensitive linkage, or a reducing environment, capable of reducing the disulfide linkage. The physical stimulus capable of cleaving the linkage may be, for example, radiation, in particular ionizing radiation.

Drug molecules in the context of the present invention include any compound with therapeutic or prophylactic effects. It can be a compound that affects or participates, for example, in tissue growth, cell growth or cell differentiation. It can also be a compound that is capable of inducing a biological action, such as an immune response.

A non-limiting list of examples includes antimicrobial agents (including antibacterial, in particular antibiotics, antiviral agents and anti-fungal agents); anti-tumor agents, in particular anticancer chemotherapeutic agents such as cytostatic(s) and cytotoxic(s); and any other biological or inorganic product intended to treat cancer, such as a therapeutic nucleic acid, in particular a microRNA (miRNA), a short-hairpin RNA (shRNA) and/or a small interfering RNA (siRNA). The drug can also be a prodrug in the context of the present invention. Any combination of drug molecules of interest may further be used.

In another embodiment, a nanoparticle wherein the hafnium oxide material is coated with a biocompatible material selected from an agent exhibiting stealth properties, an agent allowing interaction with a biological target, and a combination thereof, is herein described.

The Enhanced Permeation and Retention (EPR) effect is known to be responsible for passive accumulation of the nanoparticles in the tumor mass, after a given time following their injection by the intravenous (IV) route (one possible route of administration). It has been observed that tumor vessels are quite distinct from normal capillaries and that their vascular "leakiness" encourages selective extravasation of nanoparticles not usual in normal tissues. The lack of effective tumor lymphatic drainage prevents clearance of the penetrant nanoparticles and promotes their accumulation. The present nanoparticles are thus able to successfully target primary as well as metastatic tumors after intravenous administration.

In a preferred embodiment, the hafnium oxide material of the claimed nanoparticles can be coated with a biocompatible material selected from an agent exhibiting stealth properties. When the nanoparticles of the present invention are administered to a subject via the intravenous route, a biocompatible coating with a material selected from an agent exhibiting stealth properties is particularly advantageous to optimize the biodistribution of the nanoparticles. Said coating is responsible for the so called "stealth property" of the nanoparticles.

The agent exhibiting stealth properties may be an agent displaying a steric group. Such a group may be selected, for example, from: polyethylene glycol (PEG); polyethylenoxide; polyvinylalcohol; polyacrylate; polyacrylamide (poly (N-isopropylacrylamide)); polycarbamide; a biopolymer; a polysaccharide such as dextran, xylan and cellulose; collagen; a zwitterionic compound such as polysulfobetain; etc.

In another preferred embodiment, the hafnium oxide material of the claimed nanoparticles can be coated with a biocompatible material selected from an agent allowing interaction with a biological target. Such agent can typically bring a positive or a negative charge to the nanoparticles' surface. This charge can be determined by zeta potential measurements, typically performed on nanoparticle suspensions, the concentration of which varies between 0.2 and 10 g/L, the nanoparticles being suspended in an aqueous medium with a pH comprised between 6 and 8.

An agent forming a positive charge on the nanoparticle surface can be for example aminopropyltriethoxisilane or polylysine. An agent forming a negative charge on the nanoparticle surface can be, for example, a phosphate (for example, a polyphosphate, a metaphosphate, a pyrophosphate, etc.), a carboxylate (for example, citrate or dicarboxylic acid, in particular succinic acid) or a sulfate.

A full biocompatible coating of the nanoparticle or aggregate may be advantageous, in particular in the intravenous (IV) context, in order to avoid interaction of the particle surface with any recognition element (macrophages, opsonins, etc.). The "full coating" implies the presence of a very high density of biocompatible molecules able to create at least a complete monolayer on the surface of the particles.

The biocompatible coating allows, in particular, the nanoparticles' stability in a fluid, such as a physiological fluid (blood, plasma, serum, etc.), or any isotonic media or physiological media, for example, media comprising glucose (5%) and/or NaCl (0.9%), which is required for pharmaceutical administration.

Stability may be confirmed by dry extract quantification measured on a nanoparticle suspension prior to and after filtration, typically on a 0.22 or 0.45 µm filter.

Advantageously, the coating preserves the integrity of the particles in vivo, ensures or improves the biocompatibility thereof, and facilitates an optional functionalization thereof (for example, with spacer molecules, biocompatible polymers, targeting agents, proteins, etc.).

A particular nanoparticle according to the present invention can further comprise a targeting agent allowing its interaction with a recognition element present on the target cell. Such a targeting agent typically acts once the nanoparticles are accumulated on the target site. The targeting agent can be any biological or chemical structure displaying affinity for molecules present in the human or animal body. For instance, it can be a peptide, oligopeptide or polypeptide, a protein, a nucleic acid (DNA, RNA, SiRNA, tRNA, miRNA, etc.), a hormone, a vitamin, an enzyme, or the ligand of a molecule expressed by a pathological cell, in particular the ligand of a tumor antigen, hormone receptor, cytokine receptor or growth factor receptor. Said targeting agents can be selected, for example, from the group consisting of LHRH, EGF, a folate, anti-B-FN antibody, E-selectin/P-selectin, anti-IL-2Rα antibody, GHRH, etc.

The nanoparticles of the invention can be administered by different routes such as local (intra-tumoral (IT) in particular), subcutaneous, intravenous (IV), intradermal, intra-arterial, airway (inhalation), intraperitoneal, intramuscular and oral (per os) routes. The nanoparticles can further be administered in an intracavity, such as the virtual cavity of a tumor bed after tumorectomy.

Repeated injections or administrations of nanoparticles can be performed, when appropriate.

Another particular object of the invention relates to a pharmaceutical composition comprising nanoparticles such as defined hereinabove, preferably together with a pharmaceutically acceptable carrier or vehicle.

Another particular object of the invention relates to a diagnostic or imaging composition comprising nanoparticles such as defined hereinabove, preferably together with a physiologically acceptable carrier or vehicle.

The compositions can be in the form of a solid, liquid (particles in suspension), aerosol, gel, paste, and the like. Preferred compositions are in liquid or gel form. Particularly preferred compositions are in liquid form.

The carrier which is employed can be any classical support for this type of application, such as saline, isotonic, sterile or buffered solutions, and the like. They can also comprise stabilizers, sweeteners, surfactants, polymers and the like. They can be formulated, for example, as ampoules, aerosol, bottles, tablets, or capsules, by using known techniques of pharmaceutical formulation.

In the herein-described compositions, appropriate or desirable concentrations of nanoparticles are comprised between about $10^{-3}$ mg of nanoparticles/gram of tumor and about 100 mg of nanoparticles/gram of tumor, in particular between about 5 and about 50 mg of nanoparticles/gram of tumor. These concentrations apply whatever the route of administration.

In the herein-described compositions, appropriate or desirable concentrations of nanoparticles are comprised between about $10^{-3}$ mg of nanoparticles/mL of volume of the virtual cavity left following tumorectomy and about 100 mg of nanoparticles/mL of volume of the virtual cavity left following tumorectomy, in particular between about 5 mg and about 50 mg of nanoparticles/mL of volume of the virtual cavity left following tumorectomy. These concentrations apply whatever the route of administration.

Generally, the compositions in liquid or gel form comprise between 0.05 g/L and 400 g/L of nanoparticles, 0.05 g/L and 150 g/L, preferably at least 10 g/L, 20 g/L, 40 g/L, 45 g/L, 50 g/L, 55 g/L, 60 g/L, 80 g/L, 100 g/L, 150 g/L, 200 g/L, 250 g/L, 300 g/L or 350 g/L.

Dry extract is ideally measured following a drying step of the suspension comprising the nanoparticles.

The compositions, particles and aggregates of the invention can be used in many fields, particularly in human or veterinary medicine.

Nanoparticles and compositions according to the invention, as herein described, are preferably for use in a mammal, even more preferably in a human being, as a diagnostic agent, typically when the nanoparticle is exposed to radiation, and/or as a therapeutic agent, in particular in oncology, preferably when the nanoparticle is exposed to radiations, in particular ionizing radiation.

The terms "radiation" refers to ionizing and non-ionizing radiation. Non-ionizing radiation includes radio waves, microwaves, infrared, and visible light. Ionizing radiation includes, typically, ultraviolet light, X-rays and gamma rays.

The terms "treatment" and "therapy" refer to any action performed to correct abnormal functions, to prevent diseases, or to improve pathological signs, such as, in particular, a reduction in the size or growth of an abnormal tissue, in particular of a tumor, a control of said size or growth, a suppression or destruction of abnormal cells or tissues, a slowing of disease progression, a disease stabilization with delay of cancer progression, a reduction in the formation of metastases, a regression of a disease or a complete remission (in the context of cancer, for example), etc.

While not intending to be bound by any particular theory, the inventors believe that the claimed combination of metallic and hafnium oxide materials may be responsible, in the context of therapy, for the efficient deposit of energy within the tumor structure, when the nanoparticles are activated by radiations.

Figure 1:
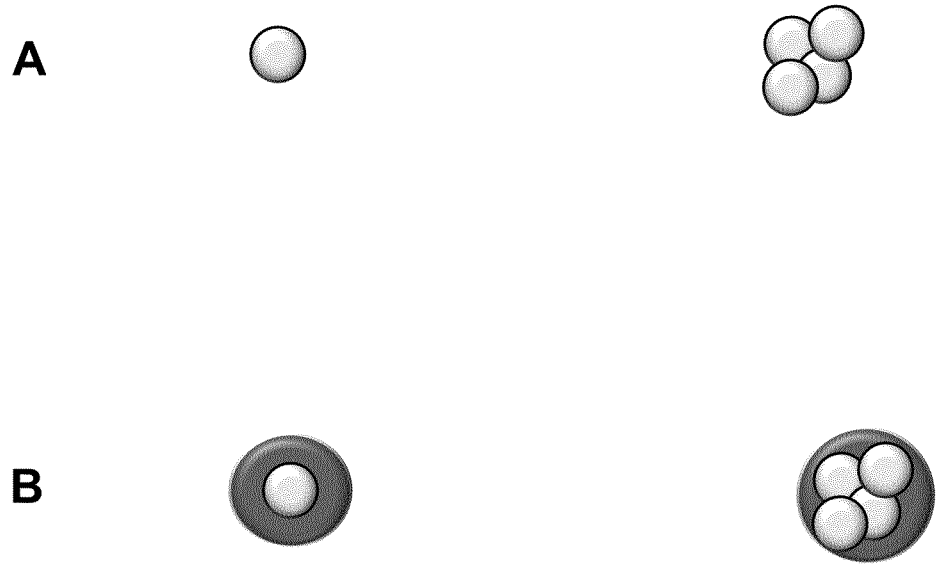
FIGS. 1A-1C provide an illustration of the inventive nanoparticle structure.
Figure 1:
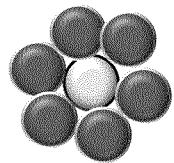
Figure 1:
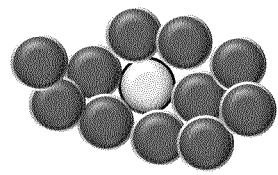
Figure 1:
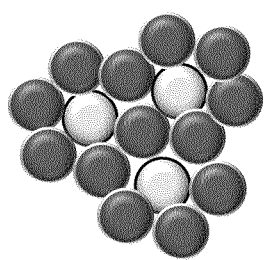
Figure 1:
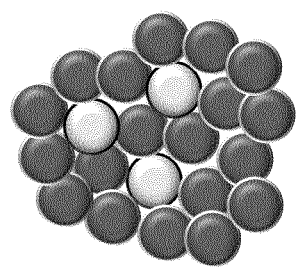
Figure 1:
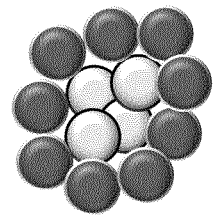
Figure 1:
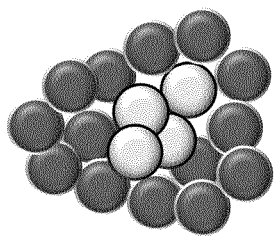
Figure 2:
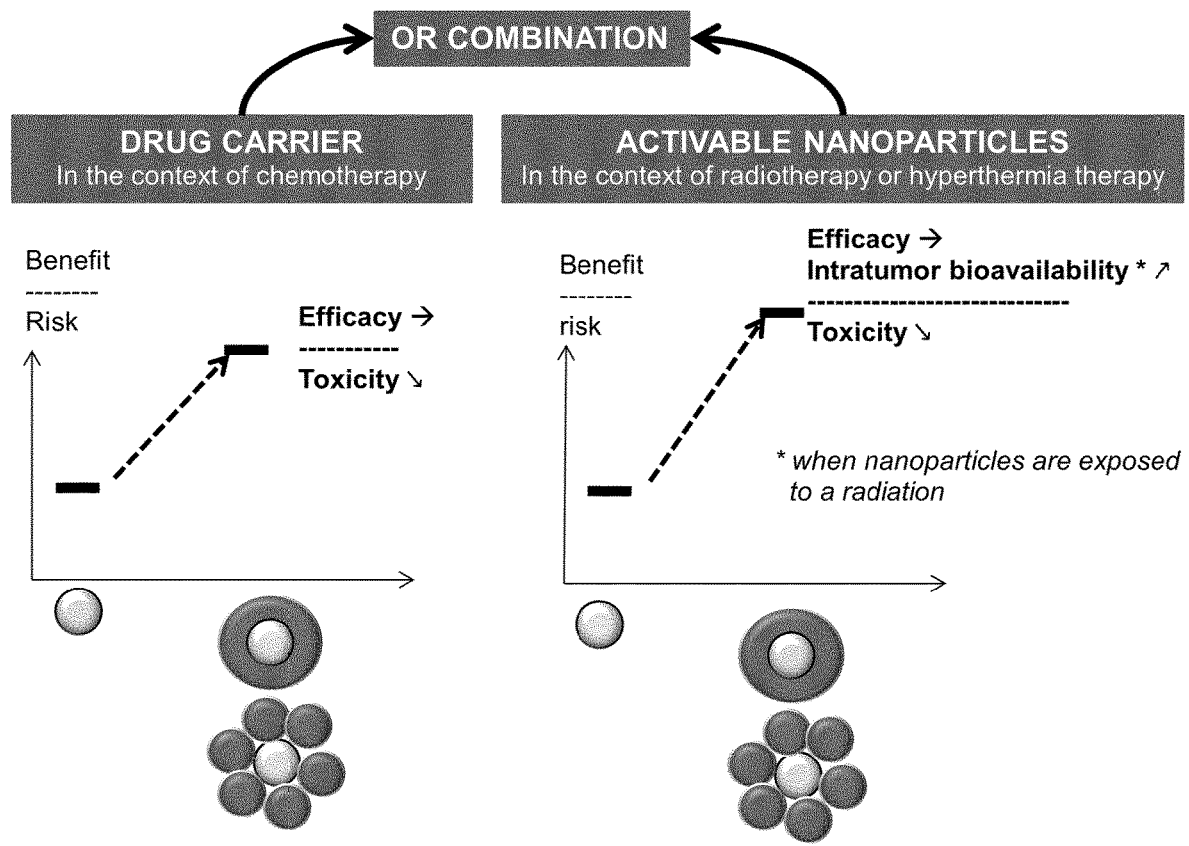
FIG. 2 provides an illustration of the benefit over risk ratio of this inventive nanoparticle structure as compared to a metallic nanoparticle deprived of hafnium oxide material, in particular in oncology, more particularly when the nanoparticle is exposed to radiations.
Figure 3:
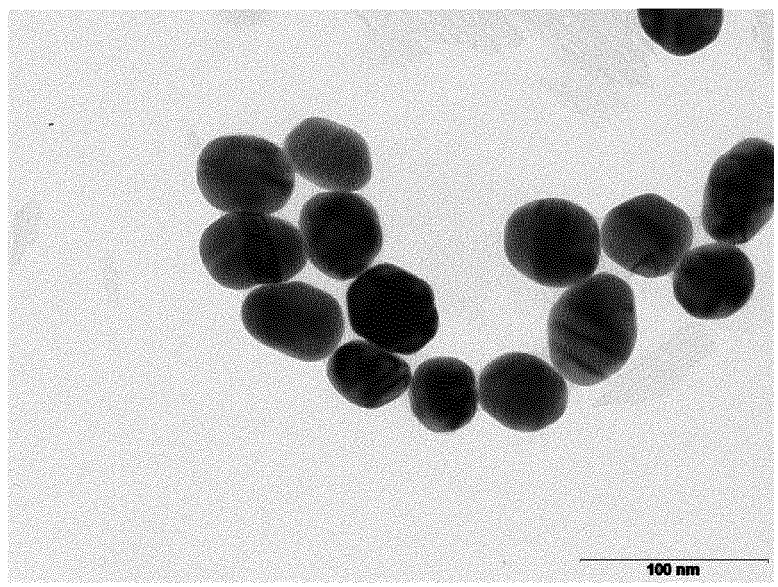
FIG. 3 provides a transmission electron microscopy picture of 60 nm-sized gold nanoparticles from example 1.

Typically, following intravenous injection, the Enhanced Permeation and Retention (EPR) effect will be responsible for passive accumulation of the nanoparticles at the tumor site. Upon the nanoparticles' activation by radiation, the deposit of energy will enhance tumor perfusion and consequently further favor the nanoparticles' intratumor penetration. The enhanced nanoparticle intratumor penetration (the nanoparticles' intratumor bioavailability) will potentiate the therapeutic activity of the inventive nanoparticles (FIG. 2).

Hence a particular object of the invention is based on the use of a nanoparticle according to the present invention to prepare a pharmaceutical composition intended to alter, destroy or eliminate target cells in an animal when said cells are exposed to radiations, in particular to ionizing radiation, and the corresponding methods.

The target cells can be any pathological cells, i.e., cells involved in a pathological mechanism, for example, proliferative cells, such as tumor cells, stenosing cells (fibroblast/smooth muscle cells), or immune system cells (pathological cell clones). A preferred application is based on the treatment (for example, the destruction or functional alteration) of malignant cells or tissue.

Another particular embodiment of the invention relates to the use of compositions or nanoparticles such as defined hereinabove for producing a pharmaceutical composition for the treatment of cancer when the nanoparticles are exposed to radiations, in particular to ionizing radiation.

The present disclosure further encompasses the use of the nanoparticles and/or compositions of the invention to prevent or treat a cancer or to alleviate the symptoms of a cancer in an animal when cells are exposed to radiations, in particular to ionizing radiation.

Classical cancer management systematically implies the concurrence of multimodality treatments (a combination of radiotherapy and chemotherapy, for example).

The herein-described nanoparticles subjected to radiations, in particular in the context of radiotherapy, can be used in association with a different cancer therapy protocol. Such a protocol can be selected from the group consisting of surgery, radiosurgery, chemotherapy, a treatment comprising administration of cytostatic(s), cytotoxic(s), a targeted therapy, a vaccine, radionuclides, in particular immunoradionuclides, and any other biological or inorganic product intended to treat cancer.

The invention can be used to treat any type of malignant tumor, such as hematological tumors or malignancies, and solid tumors, in particular of epithelial, neuroectodermal or mesenchymal origin. In addition, nanoparticles can be used to treat a premalignant lesion or a specific benign disease for which radiation therapy is classically used and/or indicated.

The invention is applicable, in the context of therapy, to primary tumors, or secondary invasions or loco-regional or distant metastases, as well as in the context of prophylaxis in order to avoid secondary malignant central nervous system involvement, such as the observed invasions (metastasis) from melanoma, lung cancer, kidney cancer, breast cancer, etc.

The nanoparticles can be used at any time throughout the anticancer treatment period. They can be administered, for example, as a neoadjuvant (before surgical intervention for cancer exeresis) or as an adjuvant (after surgery).

The nanoparticles can also be used for advanced tumors which cannot be surgically removed.

The nanoparticles herein described are in particular intended to be used to treat cancer where radiotherapy is a classical treatment. Such cancer may be selected, in particular, from the group consisting of: skin cancer, including malignant neoplasms associated with AIDS, and melanoma; central nervous system tumors including brain, brain stem, cerebellum, pituitary, spinal canal, eye and orbit; head and neck tumors; lung cancers; breast cancers; gastrointestinal tumors, such as liver and hepatobiliary tract cancers, colon, rectal and anal cancers, and stomach, pancreatic, and esophageal cancer; male genitourinary tumors such as prostate, testicular, penile and urethral cancers; gynecological tumors such as uterine cervical, endometrial, ovarian, fallopian tube, vaginal and vulvar cancers; adrenal and retroperitoneal tumors; sarcomas of bone and soft tissue, regardless of the location; lymphoma; myeloma; leukemia; and pediatric tumors such as Wilm's tumor, neuroblastoma, central nervous system tumors, Ewing's sarcoma, etc.

The nanoparticles herein described can further be used in the context of radiotherapy where their use allows a decrease of the dose of radiotherapy while keeping its efficiency in destroying tumor cells.

Under the effect of ionizing radiation, in particular X-rays, gamma rays, radioactive isotopes and/or electron beams, the nanoparticles are excited and produce electrons and/or high-energy photons. Those electrons and/or high-energy photons emitted after ionization will be responsible for direct and/or indirect cell damage, via free radical generation, and ultimately for cell destruction, resulting in a better outcome for the patient.

Depending on the energy of ionizing radiation, the nanoparticles can thus enable the destruction of tissues and/or, simply, visualization for imaging and/or for diagnostic purposes.

The particles can be excited within a large range of total doses of radiation.

Amounts and schedules (planning and delivery of irradiation in a single dose, or in the context of a fractioned or hyperfractioned protocol, etc.) are defined for any disease/anatomical site/disease stage/patient setting/patient age (child, adult, elderly patient), and constitute the standard of care for any specific situation.

The irradiation can be applied at any time after administration of the nanoparticles, on one or more occasions, by using any currently available system of radiotherapy or radiography.

As indicated previously, the appropriate radiations or sources of excitation are preferably ionizing radiation and can advantageously be selected from the group consisting of X-rays, gamma rays, electron beams, ion beams and radioactive isotopes or radioisotope emissions. X-rays are a particularly preferred source of excitation.

Ionizing radiation is typically of about 2 KeV to about 25 000 KeV, in particular of about 2 KeV to about 6000 KeV (LINAC source), or of about 2 KeV to about 1500 KeV (such as a cobalt 60 source).

In general and in a non-restrictive manner, the following X-rays can be applied in different cases to excite the particles:
  Superficial X-rays of 2 to 50 keV: to excite nanoparticles near the surface (penetration of a few millimeters);
  X-rays of 50 to 150 keV: in diagnostic and also in therapy;
  X-rays (orthovoltage) of 200 to 500 keV, which can penetrate a tissue thickness of 6 cm; and X-rays (megavoltage) of 1000 keV to 25,000 keV; for example the excitation of nanoparticles for the treatment of prostate cancer can be carried out via five focused X-rays with an energy of 15,000 keV.

Radioactive isotopes can alternatively be used as an ionizing radiation source (named as curietherapy or brachytherapy). In particular, Iodine $I^{125}$ (t ½=60.1 days), Palladium $Pd^{103}$ (t ½=17 days), Cesium $Cs^{137}$ and Iridium $Ir^{192}$ can advantageously be used.

Charged particles such as proton beams and ion beams such as carbon, in particular high-energy ion beams and/or neutron beams, can also be used as an ionizing radiation source.

Electron beams may also be used as a ionizing radiation source with energy comprised between 4 MeV and 25 MeV.

A specific monochromatic irradiation source could be used for selectively generating X-ray radiation at an energy close to or corresponding to the desired X-ray absorption edge of the atoms constituting the metallic material or the hafnium element.

Preferentially, sources of ionizing radiation may be selected from Linear Accelerator (LINAC), cobalt 60 and brachytherapy sources.

In the field of diagnostics, the inventive nanoparticles can be used as contrast agents, for detecting and/or visualizing any type of tissue. Thus, an object of the invention relates to the use of nanoparticles, such as defined hereinabove, for the detection and/or visualization of cells, tissues or organs, the nanoparticles being bioinert as such and activable (i.e., usable as diagnostic agents) when exposed to radiations generated, in particular, by radiography devices.

The present disclosure further provides kits comprising any one of the herein-described nanoparticles or compositions, as well as combinations thereof. Typically, the kit comprises at least nanoparticles according to the present invention, typically a suspension thereof. Generally, the kit further comprises one or more containers filled with one or more of the ingredients herein described of the compositions of the invention. Associated with such container(s), a labeling notice providing instructions for using the products can be provided for the nanoparticles or compositions according to the present methods.

Other aspects and advantages of the invention will become apparent in the following examples, which are given for purposes of illustration and not by way of limitation.

EXAMPLES

Example 1: Synthesis of Gold Crystallites

Gold crystallites are obtained by reduction of gold chloride ($HAuCl_4$) with sodium citrate in an aqueous solution. The protocol was adapted from G. Frens, Nature Physical Science 241 (1973) 21.

In a typical experiment, $HAuCl_4$ solution is heated to boiling. Subsequently, sodium citrate solution is added. The resulting solution is maintained under boiling for an additional period of 5 minutes.

The crystallite size may be adjusted by carefully modifying the citrate versus gold precursor ratio (see Table 1).

The as-prepared gold crystallite suspensions are then washed with water and concentrated using an ultrafiltration device (Amicon stirred cell model 8400 from Millipore) with a 30 kDa cellulose membrane, at least to a gold concentration equal to or greater than 1 g/L. The gold content is determined by ICP-MS.

The resulting suspensions are ultimately filtered through a 0.22 μm cutoff membrane filter (PES membrane from Millipore) under a laminar hood and stored at 4° C.

The gold crystallite size is determined using Transmission Electronic Microscopy (TEM) by counting more than 200 particles. Histograms are established and mean and standard deviation are reported.

TABLE 1

Typical gold crystallites obtained from reduction of gold chloride with sodium citrate. The size may be adjusted by modifying the citrate versus gold precursor ratio.

| Samples | Crystallite size | Synthesis Citrate | $HAuCl_4$ |
|---|---|---|---|
| Gold crystallite-15 | 15 ± 2 nm | 20 mL 30 mM | 500 mL 0.25 mM |
| Gold crystallite-30 | 32 ± 10 nm | 7.5 mL 40 mM | 500 mL 0.25 mM |
| Gold crystallite-60 | 60 ± 10 nm | 2 mL 85 mM | 500 mL 0.25 mM |

Example 2: Nanoparticle Suspension Comprising a Gold Material at Least Partially Covered with Hafnium Oxide Material A tetramethylammonium hydroxide (TMAOH) solution is added to a hafnium chloride ($HfCl_4$) solution. Addition of TMAOH solution is performed until the pH of the final suspension reaches a pH comprised between 7 and 13. A white precipitate is obtained.

The gold crystallite suspension from example 1 is slowly added to the white precipitate under vigorous mixing.

The resulting precipitate is further transferred to an autoclave and heated at a temperature comprised between 100° C. and 300° C. After cooling, the suspension is washed with water.

A peptization step is performed in order to get a stable suspension of nanoparticles comprising gold material at least partly embedded in hafnium oxide material.

A suspension of sodium hexametaphosphate is then added to the peptized solution and the pH of the suspension is adjusted to a pH comprised between 6 and 8.

Example 3: Gold Nanoparticles Coated with a "Linker Agent" Favoring Adhesion Between the Metal and the Hafnium Oxide Material A 10 mL suspension of gold nanoparticles of 60 nm mean diameter at a concentration of [Au]=0.1 g/L was mixed with a solution of mercaptopropyltriethoxysilane (MPTS) in ethanol (EtOH). The pH of the as-obtained suspension was adjusted to 8≤pH≤10 with a basic solution. The mixture was then heated in a stove at a temperature T≥90° C.

Example 4: Nanoparticles Comprising Gold Coated with a "Linker Agent" At Least Partially Covered with or Fully Embedded in Hafnium Oxide Material: A Core@Shell Au@$HfO_2$ Type Assembly Suspensions of gold nanoparticles coated with MPTS as a "linker agent" from example 3 were used. Typically, 500 μL of a solution of hafnium chloride ($HfCl_4$) at 20 g/L was slowly added to 5 mL of a suspension of gold nanoparticles coated with MPTS as a linker agent. The pH rapidly decreased to pH<2. It was then adjusted to 2≤pH≤4, 4<pH<8 or to 8≤pH≤10 with a basic solution. Acidic, neutral or basic pH allows modulation of the crystallinity of the hafnium oxide crystallites. The as-obtained solutions were then incubated in a stove, first at a temperature 50° C.≤T≤100° C., then at T≥100° C. in an autoclave. A core@shell Au@HfO$_2$ nanoparticle structure is obtained as shown by TEM (FIG. 6).

Example 5: Electronic Diffraction Patterns of Nanoparticles Comprising Gold at Least Partially Covered with or Fully Embedded in Hafnium Oxide Material (Au@HfO$_2$)

In order to determine the crystalline structure of the as-prepared nanoparticles, electronic diffraction was performed on two samples: gold nanoparticles from example 1 (FIG. 4) and Au@HfO$_2$ type assembly of gold nanoparticles and hafnium oxide material from example 4 (FIG. 5).

Figure 4A:
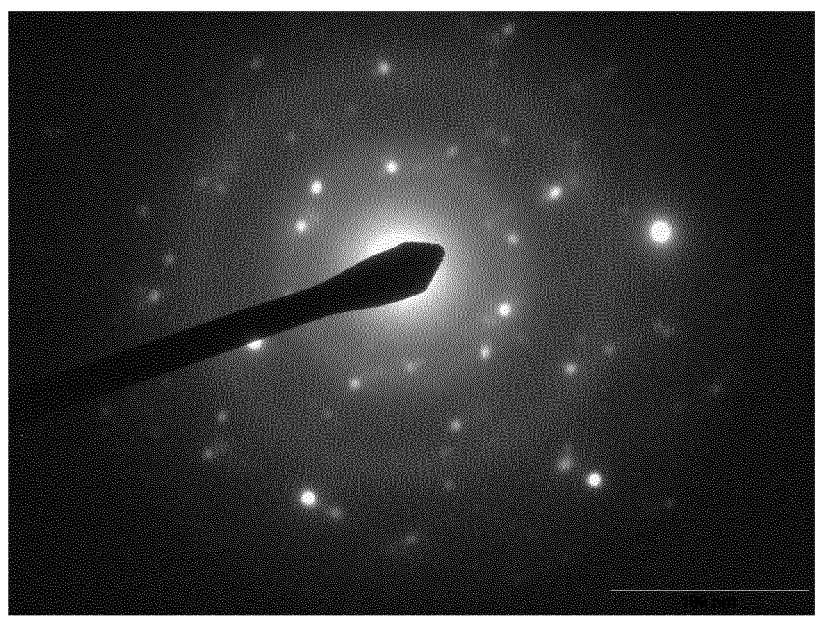

For gold nanoparticles from example 1, the crystalline structure found matches with a CFC structure with a lattice parameter $a_{experimental}$=3.984 Å (FIG. 4).

For a core@shell Au@HfO$_2$ type assembly of gold nanoparticles and hafnium oxide material from example 4 (FIG. 5), the electronic diffraction pattern shows points corresponding to interreticular distances of gold CFC crystalline structure: $d_{111}$, $d_{200}$, $d_{220}$ and $d_{311}$. An additional diffraction pattern is observed. Indexation shows three main interreticular distances, 2.798 Å, 1.599 Å and 1.316 Å, which can be attributed to diffraction plans of the HfO$_2$ monoclinic crystalline structure with a=5.12 Å, b=5.18 Å, c=5.25 Å and β=98° (reference: HfO$_2$ 00-006-0318) and which correspond to $d_{111}$, $d_{-311}$ and $d_{-223}$, respectively.

The invention claimed is:

1. A method of identifying or destroying a target cell in a mammal comprising administering a non-radioactive nanoparticle to a mammal and exposing said mammal to a radiation source, wherein the non-radioactive nanoparticle consists of a metal selected from gold (Au), silver (Ag), platinum (Pt), palladium (Pd), tin (Sn), tantalum (Ta), ytterbium (Yb), zirconium (Zr), hafnium (Hf), terbium (Tb), thulium (Tm), cerium (Ce), dysprosium (Dy), erbium (Er), europium (Eu), holmium (Ho), iron (Fe), lanthanum (La), neodymium (Nd), praseodymium (Pr), lutetium (Lu) and mixtures thereof that is fully covered with a hafnium oxide material or embedded therein and the radiation source is ionizing radiation.

2. The method according to claim 1, wherein said target cell is a tumor cell, a stenosing cell or an immune system cell.

3. The method according to claim 2, wherein said method comprises the application of a radiation source providing ionizing radiation in an amount and energy that destroys said target cell.

4. The method according to claim 1, wherein the metal is gold (Au).

5. The method according to claim 1, wherein the metal is platinum (Pt).

6. The method according to claim 1, wherein the metal is tantalum (Ta).

7. The method according to claim 1, wherein the metal is hafnium (Hf).

8. The method according to claim 1, wherein the metal is zirconium (Zr).

9. The method according to claim 1, wherein the metal is iron (Fe).

* * * * *

UNITED STATES PATENT AND TRADEMARK OFFICE
CERTIFICATE OF CORRECTION

| | |
|---|---|
| PATENT NO. | : 10,945,965 B2 |
| APPLICATION NO. | : 14/364859 |
| DATED | : March 16, 2021 |
| INVENTOR(S) | : Pottier et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 887 days.

Signed and Sealed this
Sixth Day of December, 2022

Katherine Kelly Vidal
*Director of the United States Patent and Trademark Office*